United States Patent
Kan

(10) Patent No.: US 11,198,226 B2
(45) Date of Patent: Dec. 14, 2021

(54) SURGICAL ROBOT

(71) Applicant: KAWASAKI JUKOGYO KABUSHIKI KAISHA, Kobe (JP)

(72) Inventor: Kazutoshi Kan, Kobe (JP)

(73) Assignees: KAWASAKI JUKOGYO KABUSHIKI KAISHA, Kobe (JP); MEDICAROID CORPORATION, Kobe (JP)

( * ) Notice: Subject to any disclaimer, the term of this patent is extended or adjusted under 35 U.S.C. 154(b) by 374 days.

(21) Appl. No.: 15/742,913

(22) PCT Filed: Jul. 9, 2015

(86) PCT No.: PCT/JP2015/003488
§ 371 (c)(1),
(2) Date: Jan. 9, 2018

(87) PCT Pub. No.: WO2017/006377
PCT Pub. Date: Jan. 12, 2017

(65) Prior Publication Data
US 2018/0370045 A1 Dec. 27, 2018

(51) Int. Cl.
*B25J 18/06* (2006.01)
*A61B 34/30* (2016.01)
(Continued)

(52) U.S. Cl.
CPC .............. *B25J 18/06* (2013.01); *A61B 34/30* (2016.02); *A61B 34/71* (2016.02); *B25J 9/0015* (2013.01);
(Continued)

(58) Field of Classification Search
CPC ...... B25J 18/06; B25J 18/04; B25J 9/06–065; A61B 34/71; A61B 2034/305–306;
(Continued)

(56) References Cited

U.S. PATENT DOCUMENTS

| 5,553,198 A | 9/1996 | Wang et al. |
| 5,876,325 A * | 3/1999 | Mizuno .............. A61B 1/00188 600/102 |

(Continued)

FOREIGN PATENT DOCUMENTS

| CN | 103717147 A | 4/2014 |
| EP | 2777597 A2 | 9/2014 |

(Continued)

OTHER PUBLICATIONS

Oct. 6, 2015 Search Report issued in International Patent Application No. PCT/JP2015/003488.

*Primary Examiner* — Darwin P Erezo
*Assistant Examiner* — Brigid K Byrd
(74) *Attorney, Agent, or Firm* — Oliff PLC

(57) ABSTRACT

A robot main body driving mechanism; a robot main body including a hollow flexible shaft, a joint portion including a bending joint and a proximal end continuous with a distal end of the flexible shaft, the bending joint receiving driving force of the robot main body driving mechanism to perform a bending operation, an end effector provided at a distal end of the joint portion, and a driving force transmission mechanism connecting the bending joint and the robot main body driving mechanism and configured to transmit the driving force of the robot main body driving mechanism to the bending joint; and a rotation driving mechanism configured to rotate the robot main body around an axis of a proximal end of the flexible shaft.

10 Claims, 10 Drawing Sheets

(51) Int. Cl.
*A61B 34/00* (2016.01)
*B25J 9/00* (2006.01)

(52) U.S. Cl.
CPC ......... *A61B 34/74* (2016.02); *A61B 2034/301* (2016.02); *A61B 2034/305* (2016.02)

(58) Field of Classification Search
CPC ............ A61B 2017/2929; A61B 34/30; A61B 2034/301–304; A61B 34/35; A61B 34/37; A61B 2034/715
See application file for complete search history.

(56) References Cited

U.S. PATENT DOCUMENTS

| | | | |
|---|---|---|---|
| 6,676,684 B1 * | 1/2004 | Morley | A61B 34/71 606/205 |
| 7,087,049 B2 | 8/2006 | Nowlin et al. | |
| 2002/0082612 A1 | 6/2002 | Moll et al. | |
| 2003/0040758 A1 | 2/2003 | Wang et al. | |
| 2003/0050733 A1 | 3/2003 | Wang et al. | |
| 2003/0055410 A1 | 3/2003 | Evans et al. | |
| 2003/0065311 A1 | 4/2003 | Wang et al. | |
| 2003/0135204 A1 * | 7/2003 | Lee | A61B 17/0469 606/1 |
| 2004/0176751 A1 | 9/2004 | Weitzner et al. | |
| 2004/0193146 A1 | 9/2004 | Lee et al. | |
| 2004/0199147 A1 | 10/2004 | Nishizawa et al. | |
| 2004/0236352 A1 | 11/2004 | Wang et al. | |
| 2005/0049580 A1 | 3/2005 | Brock et al. | |
| 2005/0222554 A1 * | 10/2005 | Wallace | A61B 90/50 606/1 |
| 2006/0084945 A1 * | 4/2006 | Moll | A61B 34/71 606/1 |
| 2006/0149418 A1 | 7/2006 | Anvari | |
| 2006/0253109 A1 | 11/2006 | Chu | |
| 2007/0144298 A1 | 6/2007 | Miller | |
| 2007/0260115 A1 | 11/2007 | Brock et al. | |
| 2010/0048997 A1 | 2/2010 | Okada | |
| 2010/0175701 A1 * | 7/2010 | Reis | A61B 34/30 128/852 |
| 2010/0262162 A1 | 10/2010 | Omori | |
| 2011/0028894 A1 | 2/2011 | Foley et al. | |
| 2011/0144656 A1 | 6/2011 | Lee et al. | |
| 2011/0282355 A1 | 11/2011 | Lee et al. | |
| 2013/0110128 A1 | 5/2013 | Schostek et al. | |
| 2013/0304084 A1 | 11/2013 | Beira et al. | |
| 2014/0330288 A1 | 11/2014 | Date et al. | |
| 2015/0088160 A1 | 3/2015 | Kwon | |
| 2015/0313619 A1 | 11/2015 | Tadano et al. | |
| 2016/0135662 A1 | 5/2016 | Hatakeyama et al. | |

FOREIGN PATENT DOCUMENTS

| | | |
|---|---|---|
| JP | H07-328024 A | 12/1995 |
| JP | H08-107898 A | 4/1996 |
| JP | H08-280695 A | 10/1996 |
| JP | 2002-500524 A | 1/2002 |
| JP | 2004-504095 A | 2/2004 |
| JP | 2004-122286 A | 4/2004 |
| JP | 2007-167643 A | 7/2007 |
| JP | 2007-167644 A | 7/2007 |
| JP | 2007-325959 A | 12/2007 |
| JP | 2008-284214 A | 11/2008 |
| JP | 2009-509653 A | 3/2009 |
| JP | 2009-509654 A | 3/2009 |
| JP | 2010-178988 A | 8/2010 |
| JP | 2010-214166 A | 9/2010 |
| JP | 2011-194247 A | 10/2011 |
| JP | 2012-125589 A | 7/2012 |
| JP | 2012-152583 A | 8/2012 |
| JP | 2012-254360 A | 12/2012 |
| JP | 2013-027733 A | 2/2013 |
| JP | 2013-094672 A | 5/2013 |
| JP | 2013-135862 A | 7/2013 |
| JP | 2013-138965 A | 7/2013 |
| JP | 2014-076361 A | 5/2014 |
| JP | 2014-111080 A | 6/2014 |
| JP | 2014-111081 A | 6/2014 |
| JP | 2014-180751 A | 9/2014 |
| JP | 2014-531219 A | 11/2014 |
| JP | 2015-006423 A | 1/2015 |
| JP | 2015-501729 A | 1/2015 |
| WO | 02/07608 A2 | 1/2002 |
| WO | 02/065933 A2 | 8/2002 |
| WO | 2011/153082 A2 | 12/2011 |
| WO | 2012/027615 A2 | 3/2012 |
| WO | 2012/033629 A2 | 3/2012 |
| WO | 2012/044590 A2 | 4/2012 |
| WO | 2012/166499 A1 | 12/2012 |
| WO | 2013/009887 A1 | 1/2013 |
| WO | 2013/067535 A1 | 5/2013 |
| WO | 2014/069003 A1 | 5/2014 |
| WO | 2014/151621 A1 | 9/2014 |
| WO | 2015/012150 A1 | 1/2015 |

* cited by examiner

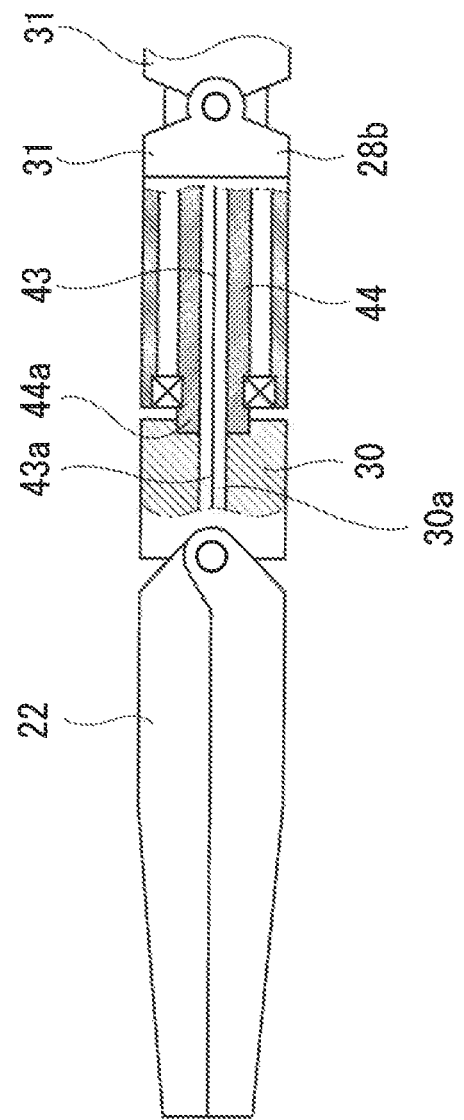

SURGICAL ROBOT

TECHNICAL FIELD

The present invention relates to a surgical robot.

BACKGROUND ART

A medical manipulator system has been known (see PTL 1, for example).

The manipulator system includes: a manipulator including a holding portion at a tip end portion thereof, the holding portion holding suture thread, a needle, etc.; a manipulator main body; and an arm including one end to which the manipulator is attached. An axially intermediate portion of the arm is attached to the manipulator main body through a gimbal portion. The other end of the arm is attached to the manipulator main body through a gimbal portion. The manipulator main body operates the gimbal portion at the other end of the arm to move a tip end of the arm with the gimbal portion at the axially intermediate portion of the arm as a fulcrum. Thus, the holding portion of the manipulator is moved.

CITATION LIST

Patent Literature

PTL 1: Japanese Laid-Open Patent Application Publication No. 2004-122286

SUMMARY OF INVENTION

Technical Problem

However, the manipulator system described in PTL 1 has problems in which a mechanism for moving the holding portion of the manipulator is a large-scale mechanism, and this is disadvantageous in manufacture and increases manufacturing cost.

Solution to Problem

To solve the above problems, a surgical robot according to one aspect of the present invention includes: a robot main body driving mechanism; a robot main body including a hollow flexible shaft, a joint portion including a bending joint and a proximal end continuous with a distal end of the flexible shaft, the bending joint receiving driving force of the robot main body driving mechanism to perform a bending operation, an end effector provided at a distal end of the joint portion, and a driving force transmission mechanism connecting the bending joint and the robot main body driving mechanism and configured to transmit the driving force of the robot main body driving mechanism to the bending joint; and a rotation driving mechanism configured to rotate the robot main body around an axis of a proximal end of the flexible shaft.

According to this configuration, by rotating the robot main body around the axis of the proximal end of the flexible shaft by the rotation driving mechanism, the end effector can be moved in a circumferential direction about an axis of the distal end of the flexible shaft. Therefore, the surgical robot can be reduced in size, and the manufacturing cost of the surgical robot can be made low.

The rotation driving mechanism may rotate the robot main body and the robot main body driving mechanism integrally around the axis of the proximal end of the flexible shaft.

According to this configuration, the robot main body can be rotated around the axis of the proximal end of the flexible shaft by a simple configuration.

The surgical robot may include a translation driving mechanism configured to translate the robot main body in a direction along the axis of the proximal end of the flexible shaft.

According to this configuration, the end effector can be moved in a direction along the axis of the distal end of the flexible shaft.

The translation driving mechanism may translate the robot main body and the robot main body driving mechanism integrally in the direction along the axis of the proximal end of the flexible shaft.

According to this configuration, the robot main body can be translated in the direction along the axis of the distal end of the flexible shaft by a simple configuration.

The surgical robot may be configured such that: the joint portion includes a first bending joint and a second bending joint; the first bending joint receives the driving force of the robot main body driving mechanism to perform the bending operation in a predetermined direction; and the second bending joint receives the driving force of the robot main body driving mechanism to perform the bending operation in a direction opposite to the direction in which the first bending joint performs the bending operation.

According to this configuration, the posture of the end effector can be directed toward an inside, and operations can be easily performed.

The end effector may be a pair of forceps.

According to this configuration, the surgical robot can be used in an operation using the forceps.

The surgical robot may further include a surgical robot support base configured to be attachable to a support rail provided at an operating table, wherein the rotation driving mechanism may be supported by the surgical robot support base.

According to this configuration, surgery can be performed with the surgical robot located near a patient, and a distance between an operator and the patient can be shortened.

Advantageous Effects of Invention

The present invention has effects of being able to reduce the size of the surgical robot and lower the manufacturing cost of the surgical robot.

BRIEF DESCRIPTION OF DRAWINGS

FIG. 4 is a partial breakaway view showing a configuration example of a wrist joint of the robot main body of the surgical robot of FIG. 1.

DESCRIPTION OF EMBODIMENTS

Hereinafter, an embodiment of the present invention will be explained in reference to the drawings. It should be noted that the present invention is not limited by the present embodiment. In the following explanations and the drawings, the same reference signs are used for the same or corresponding components, and a repetition of the same explanation is avoided.

Figure 1:
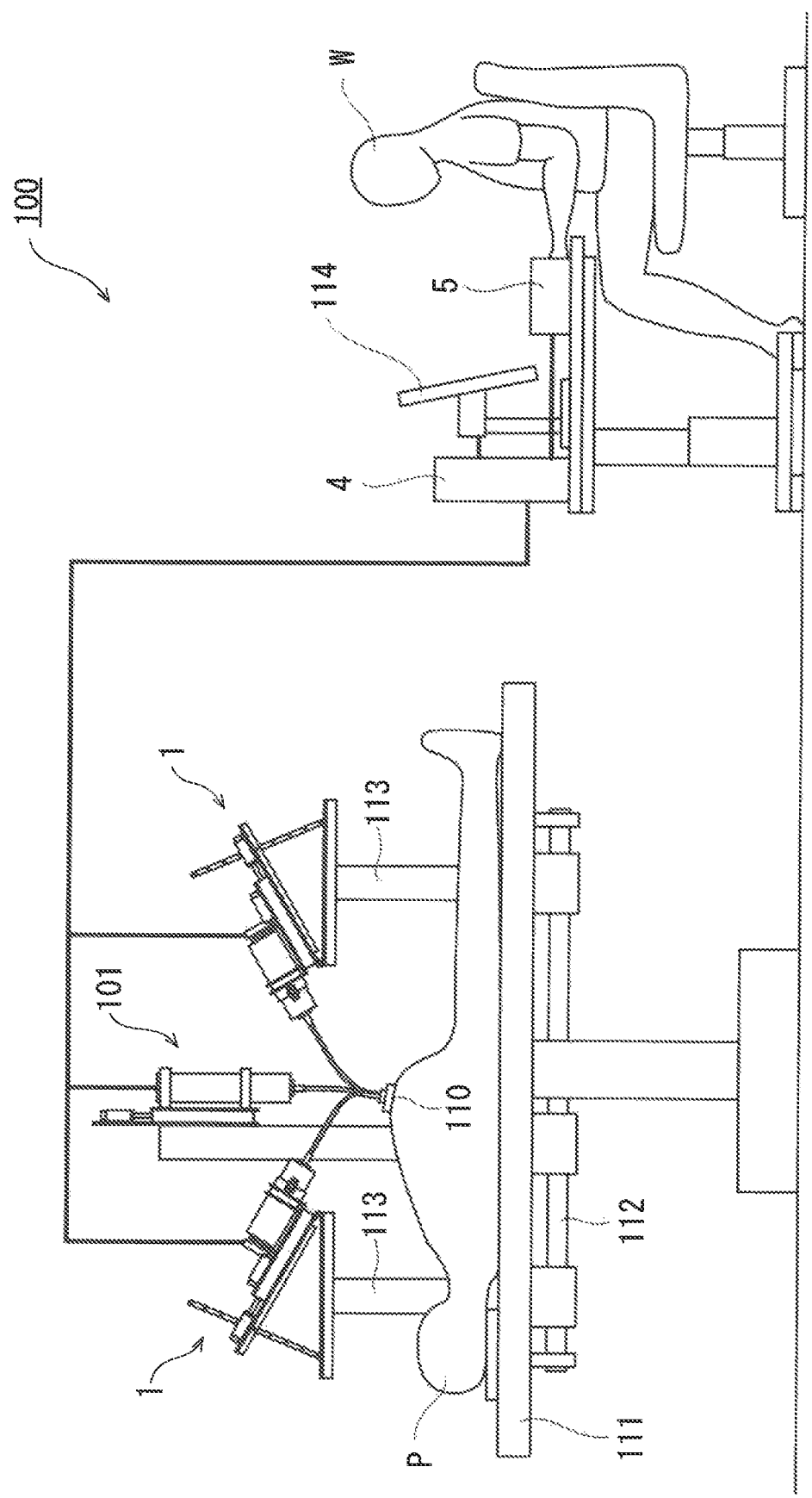
FIG. 1 is a diagram schematically showing a configuration example of a surgical robot system including a surgical robot according to an embodiment of the present invention.
Figure 2:
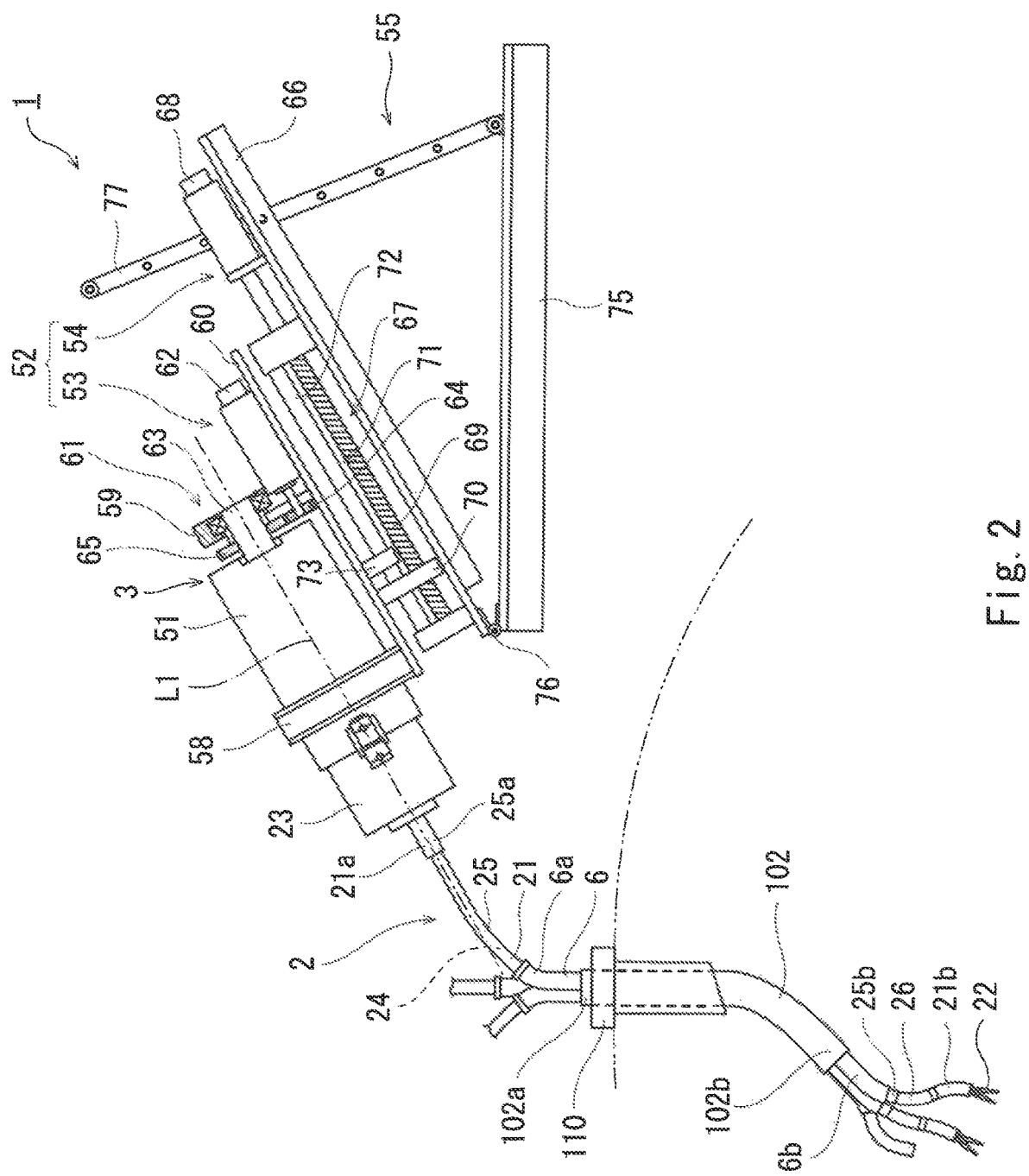
FIG. 2 is a diagram showing a configuration example of the surgical robot of FIG. 1.

FIG. 1 is a diagram schematically showing a configuration example of a surgical robot system 100 including a surgical robot 1 according to the embodiment of the present invention. FIG. 2 is a diagram showing a configuration example of the surgical robot 1.

As shown in FIG. 1, the surgical robot system 100 is a system used when an operator W remotely operates a surgical tool from an outside to perform minimally invasive surgery, the surgical tool being provided at a distal end of the surgical robot 1 and inserted into a body of a patient P on an operating table 111.

For example, the surgical robot system 100 includes one or more surgical robots 1 and an endoscope 101.

The surgical robot 1 is supported by a surgical robot support base 113 attached to a support rail 112 provided at the operating table 111. The surgical robot 1 includes an arm formed in a thin and long shape and further includes a surgical tool at a distal end of the arm. A treated part in the body of the patient P is treated by the surgical tool. In the present embodiment, the surgical robot 1 is a robot including a pair of forceps at the distal end of the arm. However, the surgical tool at the distal end of the arm is not limited to the forceps, and various surgical tools are applicable.

The endoscope 101 is used by the operator W to visually recognize the inside of the body of the patient and includes a video camera and a light at a distal end of the endoscope 101. An image taken by the video camera of the endoscope 101 is displayed on a display device 114. With this, the operator W can operate the surgical robot 1 to perform surgery while visually recognizing states of the distal end of the arm of the surgical robot 1 and the surgical tool in the body of the patient P and a state of the treated part.

As shown in FIG. 2, the surgical robots 1 are inserted into a collectively bundling pipe 102 to be collectively bundled.

The collectively bundling pipe 102 has flexibility and is formed in a hollow tubular shape.

Configuration Example of Robot Main Body

Figure 3A:
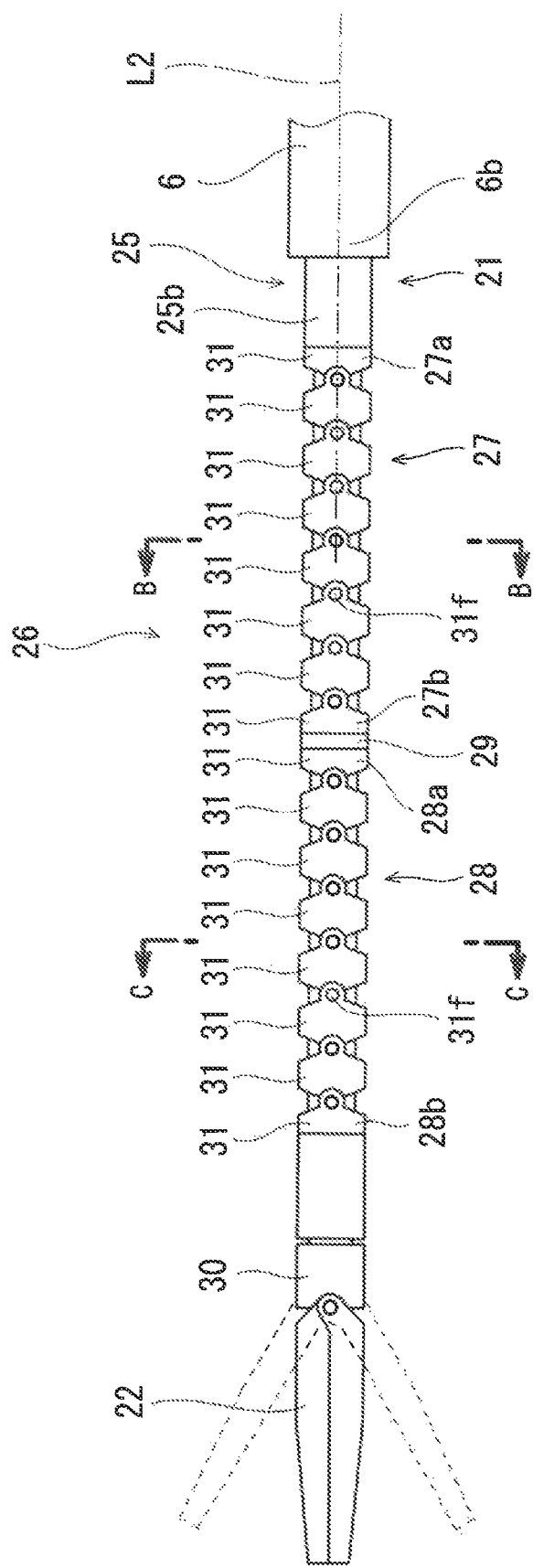
FIG. 3A is a diagram showing a configuration example of a distal end of a robot main body of the surgical robot of FIG. 1 and is a diagram showing a state where a joint portion of the robot main body is linearly stretched.
Figure 3B:
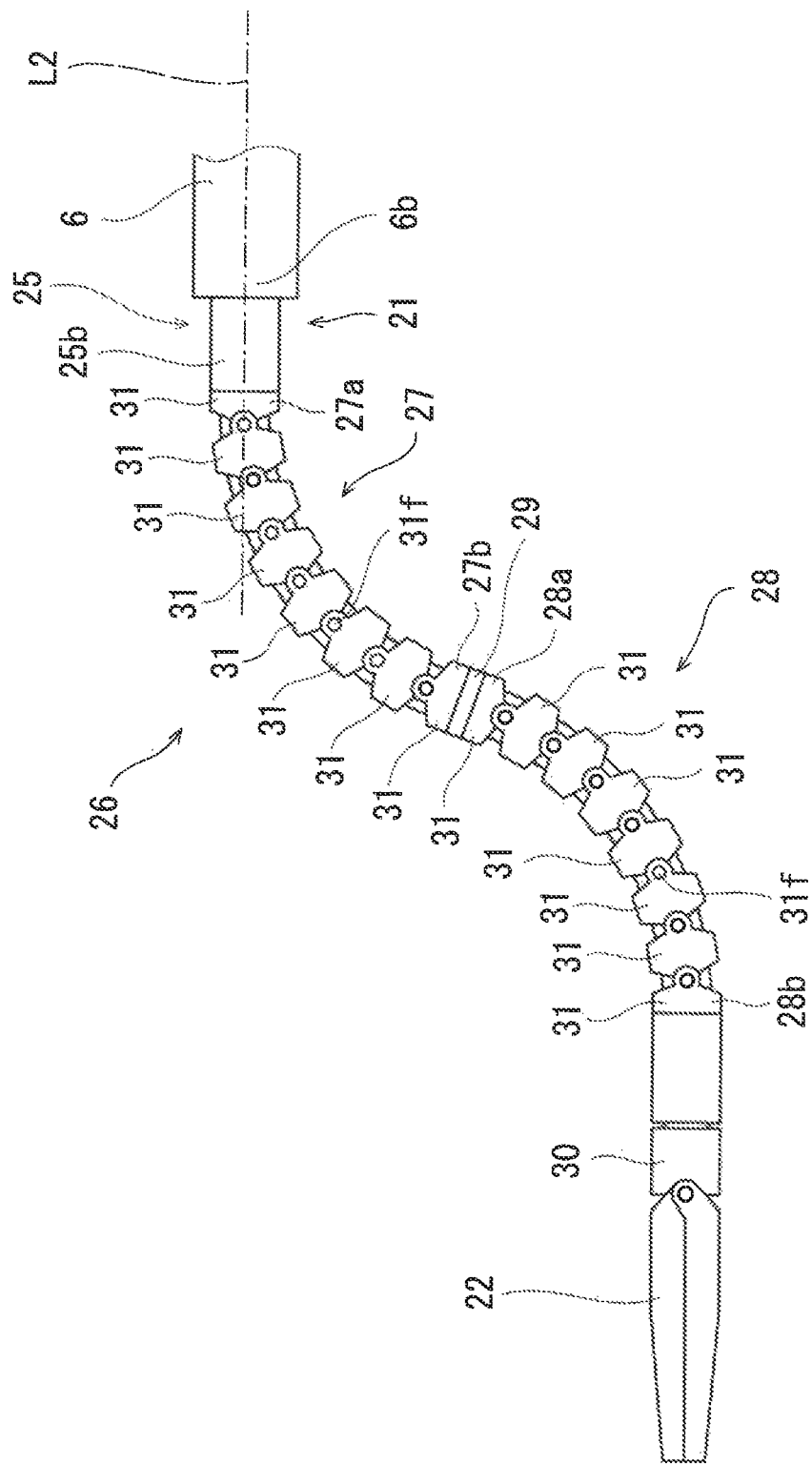
FIG. 3B is a diagram showing a configuration example of the distal end of the robot main body of the surgical robot of FIG. 1 and is a diagram showing a state where the joint portion of the robot main body is bent.

FIG. 3A is a diagram showing a configuration example of a distal end of a robot main body 2 and is a diagram showing a state where a joint portion of the robot main body 2 is linearly stretched. FIG. 3B is a diagram showing a configuration example of the distal end of the robot main body 2 and is a diagram showing a state where the joint portion of the robot main body 2 is bent.

As shown in FIG. 2, the surgical robot 1 includes the robot main body 2, a driving portion 3, a control unit 4 (see FIG. 1), and an operating portion 5 (see FIG. 1). Further, in the present embodiment, the surgical robot 1 includes a guide pipe 6.

As shown in FIG. 2, the robot main body 2 includes an arm 21, an end effector provided at a distal end 21b of the arm 21, and a driving force transmission mechanism 24. Further, the robot main body 2 includes a base 23. The base 23 is configured to be attachable to the driving portion 3. By attaching the base 23 to the driving portion 3, the robot main body 2 can be coupled to the driving portion 3.

As shown in FIGS. 3A and 3B, the arm 21 includes a hollow flexible shaft 25 having flexibility and a joint portion 26.

The flexible shaft 25 is, for example, a tubular body. As shown in FIG. 2, a proximal end 25a of the flexible shaft 25 is attached and fixed to the base 23.

The flexible shaft 25 has flexibility in a bending direction and high rigidity in an axial direction. Further, the flexible shaft 25 has rigidity to rotational torque around an axis.

A proximal end of the joint portion 26 (i.e., a proximal end 27a of a first bending joint 27) is continuous with a distal end 25b of the flexible shaft 25. The joint portion 26 is a hollow tubular body, and an internal space of the joint portion 26 communicates with an internal space of the flexible shaft 25.

The joint portion 26 includes the first bending joint 27, a second bending joint 28, a connecting portion 29, and a wrist joint 30. The first bending joint 27, the second bending joint 28, the connecting portion 29, and the wrist joint 30 are arranged on the same axis. An outer peripheral surface of the joint portion 26 is covered with a cover (not shown), and the joint portion 26 is substantially the same in diameter as the flexible shaft 25.

The first bending joint 27 is a hollow tubular body, and the proximal end 27a thereof is attached to the distal end 25b of the flexible shaft 25 so as to be continuous with the distal end 25b. It should be noted that the term "continuous" denotes not only a case where two members are directly connected to each other but also a case where two members are indirectly connected to each other with another member interposed therebetween.

Figure 6A:
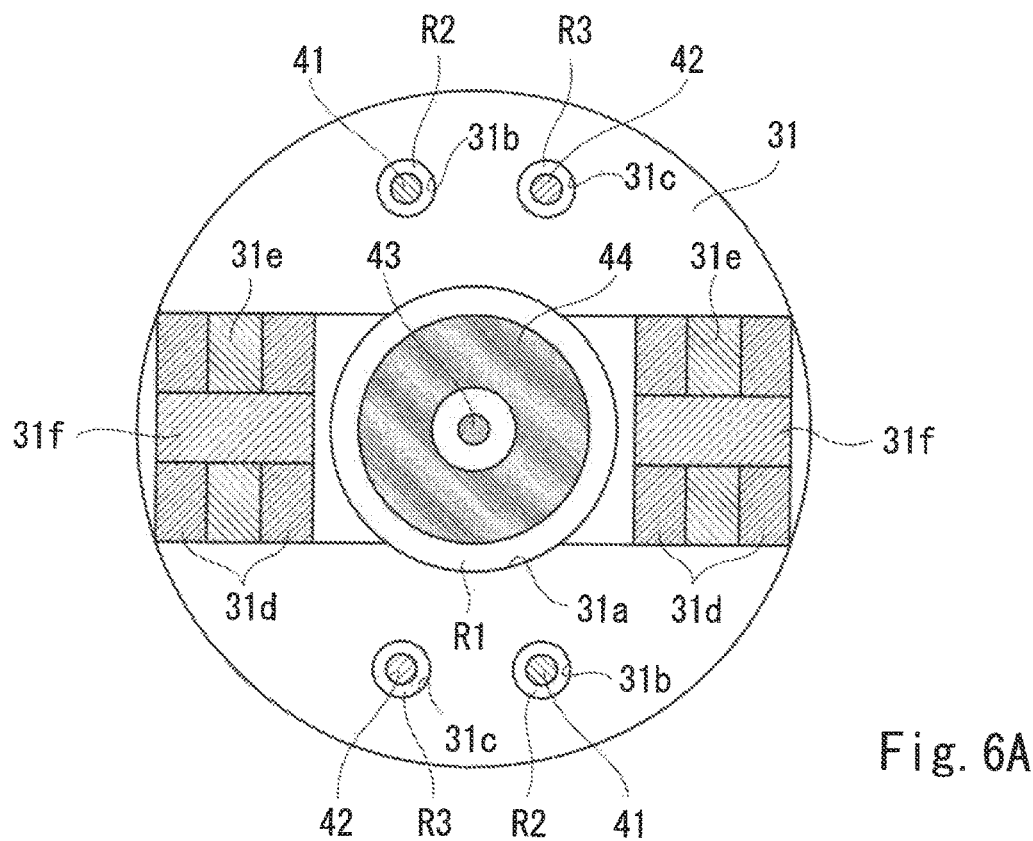
FIG. 6A is a B-B arrow view showing a configuration example of the distal end of the robot main body of the surgical robot of FIG. 1.
Figure 6B:
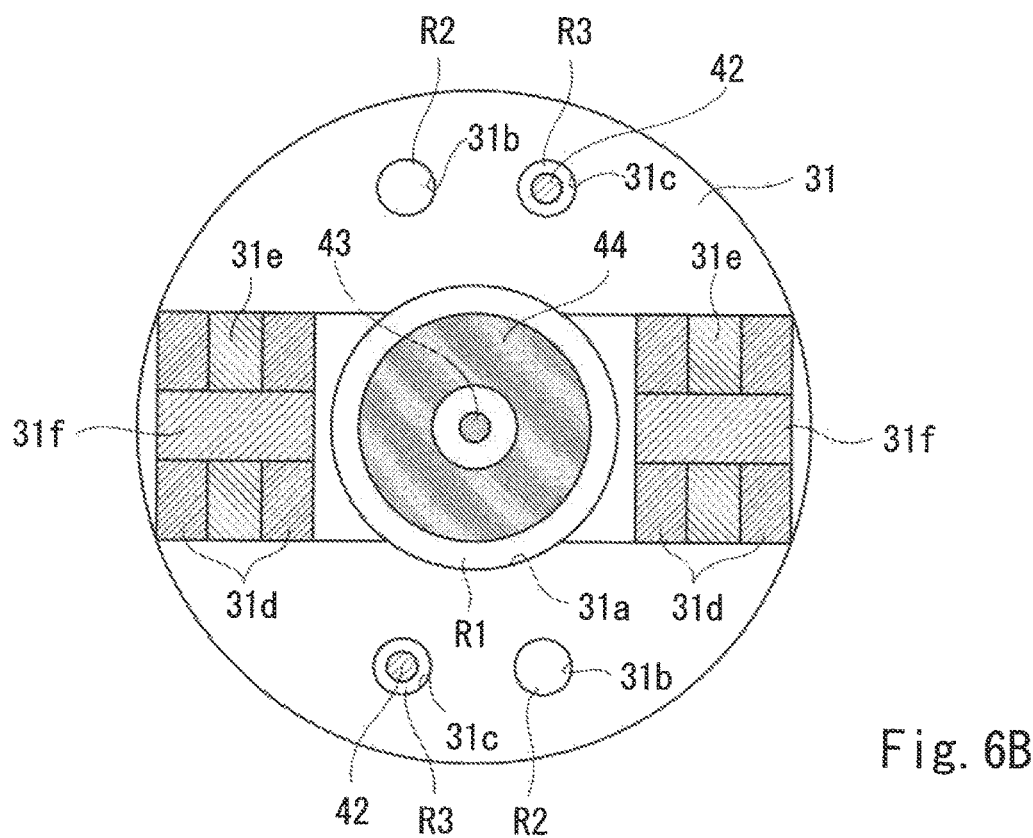
FIG. 6B is a C-C arrow view showing a configuration example of the distal end of the robot main body of the surgical robot of FIG. 1.

FIG. 6A is a B-B arrow view showing a configuration example of the distal end of the robot main body 2. FIG. 6B is a C-C arrow view showing a configuration example of the distal end of the robot main body 2.

The first bending joint 27 includes a plurality of frame members 31 that are continuous in a row in an axial direction of the joint portion 26. Each of the frame members 31 is formed in a columnar shape extending in the axial direction of the joint portion 26. The frame member 31 is formed in such a tapered shape that when viewed from a direction perpendicular to an axis of the frame member 31 and a bending direction of the below-described first bending joint 27 (i.e., when viewed from an extending direction of a below-described pin 310), a thickness of the frame member 31 in an axial direction decreases as the frame member 31 extends away from the axis of the frame member 31. To be specific, the frame member 31 is formed so as to be thinner as it extends upward and downward in FIG. 3A. With this, interference between opposing end surfaces of the adjacent frame members 31 when the first bending joint 27 is bent is avoided.

As shown in FIGS. 6A and 6B, the frame member 31 includes a first insertion hole 31a, a pair of second insertion holes 31b, and a pair of third insertion holes 31c.

The first insertion hole 31a is formed on the axis of the frame member 31, and a below-described torque transmission tube 44 is inserted through the first insertion hole 31a. The first insertion holes 31a of the plurality of frame members 31 that are continuous in a row constitute a first route R1 extending in an extending direction of the arm 21.

The pair of second insertion holes 31b connect both end surfaces of the frame member 31 and extend parallel to the axis of the frame member 31. When viewed from the direction perpendicular to the axis of the frame member 31 and the bending direction of the below-described first bending joint 27 (i.e., when viewed from the extending direction of the below-described pin 31f), one of the pair of second insertion holes 31b is located at an opposite side of the other of the pair of second insertion holes 31b across the axis of the frame member 31. To be specific, in FIG. 3A, one of the pair of second insertion holes 31b is formed above the below-described pin 31f, and the other is formed under the below-described pin 31f. Both end portions of a below-described first bending joint operating cable 41 are inserted through the respective second insertion holes 31b. The pairs of second insertion holes 31b of the plurality of frame members 31 that are continuous in a row constitute a pair of second routes R2 extending in the extending direction of the arm 21. Therefore, when viewed from the extending direction of the below-described pin 31f, one of the pair of second routes R2 is located at an opposite side of the other of the pair of second routes R2 across the axis of the frame member 31.

The pair of third insertion holes 31c connect both end surfaces of the frame member 31 and extend parallel to the axis of the frame member 31. When viewed from the direction perpendicular to the axis of the frame member 31 and the bending direction of the below-described first bending joint 27, one of the pair of third insertion holes 31c is located at an opposite side of the other of the pair of third insertion holes 31c across the axis of the frame member 31. To be specific, in FIG. 3A, one of the pair of third insertion holes 31c is formed above the below-described pin 31f, and the other is formed under the below-described pin 31f. Both end portions of a below-described second bending joint operating cable 42 are inserted through the respective third insertion holes 31c. The pairs of third insertion holes 31c of the plurality of frame members 31 that are continuous in a row constitute a pair of third routes R3 extending in the extending direction of the arm 21. Therefore, when viewed from the extending direction of the below-described pin 31f, one of the pair of third routes R3 is located at an opposite side of the other of the pair of third routes R3 across the axis of the frame member 31.

A pair of first projecting portions 31d are formed to project from one of the end surfaces of the frame member 31 outward in an extending direction of the frame member 31, and a pair of second projecting portions 31e are formed to project from the other end surface of the frame member 31 outward in the extending direction of the frame member 31. The pair of first projecting portions 31d of the frame member 31 and the pair of second projecting portions 31e of the adjacent frame member 31 are coupled to each other by a pair of pins 31f lined up on the same straight line. With this, each frame member 31 is coupled to the adjacent frame member 31 so as to be swingable about an axis (swing axis) of the pair of pins 31f. The swing axes of the frame members 31 are parallel to one another, and the first bending joint 27 performs such a bending operation that a distal end 27b of the first bending joint 27 turns toward a direction (hereinafter also referred to as the bending direction) perpendicular to the axis of the frame member 31 and the swing axis. In FIG. 3A, the axis of the frame member 31 denotes an axis extending in a paper surface leftward/rightward direction, and the swing axis denotes an axis extending in a paper surface depth direction.

As described above, when viewed from the extending direction of the below-described pin 31f, one of the pair of second routes R2 is located at an opposite side of the other of the pair of second routes R2 across the axis of the frame member 31. Therefore, when the first bending joint 27 performs the bending operation, the route length of the second route R2 located at a bending-direction inner side out of the pair of second routes R2 becomes short, and the route length of the second route R2 located at a bending-direction outer side becomes long. Similarly, when viewed from the extending direction of the below-described pin 31f, one of the pair of third routes R3 is located at an opposite side of the other of the pair of third routes R3 across the axis of the frame member 31. Therefore, when the first bending joint 27 performs the bending operation, the route length of the third route R3 located at the bending-direction inner side out of the pair of third routes R3 becomes short, and the route length of the third route R3 located at the bending-direction outer side becomes long.

Since the second bending joint 28 is the same in configuration as the first bending joint 27, an explanation thereof is omitted.

The connecting portion 29 is a hollow tubular body and connects the first bending joint 27 and the second bending joint 28.

The first bending joint 27 and the second bending joint 28 are configured to perform the respective bending operations on the same plane. Therefore, as shown in FIG. 3A, in a state where the first bending joint 27 and the second bending joint 28 are linearly stretched, the forceps 22 can hold a target from a front side of the target. Further, as shown in FIG. 3B, by bending the first bending joint 27 and the second bending joint 28, a pair of forceps 22 can be moved in a radial direction about an axis L2 of the distal end 25b of the flexible shaft 25. For example, when the forceps 22 is turned from this state toward the axis L2, the forceps 22 can hold an outer peripheral edge of the target from a lateral side of the target.

The wrist joint 30 rotates the forceps 22 around an axis of the arm 21. The wrist joint 30 is a plate-shaped body extending on a plane perpendicular to the axis of the arm 21 (joint portion 26) and is provided with a through hole 30a at a center portion of the wrist joint 30. The through hole 30a is a hole through which a below-described forceps operating cable 43 is inserted. The through hole 30a is formed on the axis of the arm 21. The wrist joint 30 is attached to a distal end 28b of the second bending joint 28 through a bearing (not shown) so as to be continuous with the distal end 28b and rotatable around the axis of the arm 21. Therefore, the wrist joint 30 is configured to be rotatable around an axis of the distal end 21b of the arm 21 relative to the flexible shaft 25, the first bending joint 27, and the second bending joint 28.

A distal end 44a of the below-described torque transmission tube 44 is fixed to a proximal end surface of the wrist joint 30, i.e., a peripheral portion of the through hole 30a (see FIG. 4). Therefore, by rotating a proximal end of the torque transmission tube 44, the distal end 44a of the torque transmission tube 44 is rotated, and this rotates the wrist joint 30.

The end effector is a surgical tool. In the present embodiment, the end effector is the forceps 22. The forceps 22 is attached to the wrist joint 30. To be specific, the forceps 22 is continuous with a distal end of the joint portion 26 (i.e., the distal end 28b of the second bending joint 28). Therefore, by rotating the proximal end of the torque transmission tube 44, the forceps 22 is rotated around the axis of the arm 21 (joint portion 26) through the wrist joint 30. With this, the posture of the forceps 22 can be adjusted in accordance with the posture of the target, and the forceps 22 can hold the target.

The forceps 22 includes an opening/closing operation operating mechanism (not shown) including an operating cable coupling portion. The operating cable coupling portion is a portion to which a distal end 43a of the below-described forceps operating cable 43 is coupled. The opening/closing operation operating mechanism of the forceps 22 is a mechanism configured to, when the operating cable coupling portion is moved in a predetermined direction, open or close the forceps by a predetermined amount in accordance with a movement distance of the operating cable coupling portion. The operating cable coupling portion is biased by a biasing mechanism (not shown) in a direction from a proximal end of the forceps operating cable 43 toward the distal end 43a. With this, when the forceps operating cable 43 is pulled in a direction from the distal end 43a to the proximal end, the operating cable coupling portion is moved in a movement direction of the distal end 43a of the forceps operating cable 43 against the biasing force of the biasing mechanism. Thus, the forceps 22 performs, for example, a closing operation to perform a holding operation of the target. Further, when the forceps operating cable 43 is sent out in a direction from the proximal end to the distal end 43a, the forceps operating cable 43 is slackened. However, the biasing mechanism moves the operating cable coupling portion in a direction opposite to the movement direction of the distal end 43a of the forceps operating cable 43 so as to absorb the slackening of the forceps operating cable 43. Thus, the forceps 22 performs, for example, an opening operation to perform a releasing operation of the target.

As above, an internal space from a proximal end 21a of the arm 21 to the distal end 21b is a communicating space, and the first bending joint operating cable 41, the second bending joint operating cable 42, the forceps operating cable 43, and the torque transmission tube 44 in the below-described driving force transmission mechanism 24 are inserted through this internal space.

The driving force transmission mechanism 24 is a mechanism configured to transmit driving force of a below-described robot main body driving mechanism 51 of the driving portion 3 to mechanisms that are continuous with the distal end 25b of the flexible shaft 25. To be specific, the driving force transmission mechanism 24 is a mechanism configured to: connect between the robot main body driving mechanism 51 and the first bending joint 27, between the robot main body driving mechanism 51 and the second bending joint 28, between the robot main body driving mechanism 51 and the wrist joint 30, and between the robot main body driving mechanism 51 and the forceps 22; and transmit the driving force of the robot main body driving mechanism 51 to the first bending joint 27, the second bending joint 28, the wrist joint 30, and the forceps 22. As shown in FIGS. 3 and 4, the driving force transmission mechanism 24 includes the first bending joint operating cable 41, a first bending joint operating cable operating portion (not shown), the second bending joint operating cable 42, a second bending joint operating cable operating portion (not shown), the forceps operating cable 43, a forceps operating cable operating portion (not shown), the torque transmission tube 44, and a torque transmission tube rotating portion (not shown).

Figure 5A:
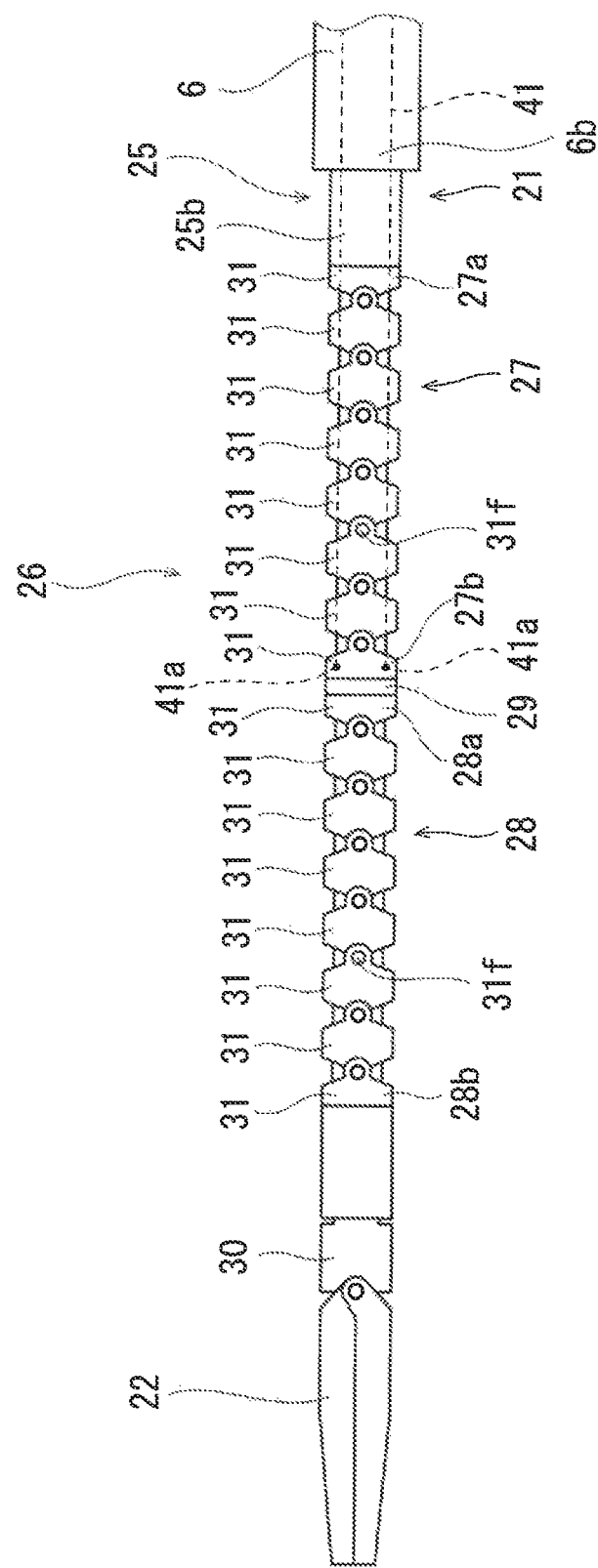
FIG. 5A is a diagram showing a configuration example of the distal end of the robot main body of the surgical robot of FIG. 1 and is a diagram showing a configuration example of a first bending joint operating cable.

FIG. 5A is a diagram showing a configuration example of the distal end of the robot main body 2 and is a diagram showing a configuration example of the first bending joint operating cable 41.

As shown in FIG. 5A, both end portions 41a of the first bending joint operating cable 41 are fixed to the frame member 31 located at the distal end 27b of the first bending joint 27.

A part of the first bending joint operating cable 41 which part extends from one of the end portions 41a to an intermediate portion of the first bending joint operating cable 41 extends through an internal space of one of the pair of second routes R2 of the first bending joint 27 and the internal space of the flexible shaft 25 to reach the internal space of the base 23. Further, a part of the first bending joint operating cable 41 which part extends from the other end portion 41a to the intermediate portion extends through an internal space of the other of the pair of second routes R2 of the first bending joint 27 and the internal space of the flexible shaft 25 to reach an internal space of the base 23.

The first bending joint operating cable operating portion is a mechanism provided in the base 23 and configured to move the intermediate portion of the first bending joint operating cable 41 in an extending direction of the first bending joint operating cable 41 by the driving force of the driving portion 3, the intermediate portion being located in the internal space of the base 23. When the intermediate portion of the first bending joint operating cable 41 is moved toward one side in the extending direction of the first bending joint operating cable 41 by the driving force of the driving portion 3, a part of the first bending joint operating cable 41 which part extends from the intermediate portion to one of the end portions 41a is pulled, and the one end portion 41a moves toward the proximal end 21a of the arm 21. With this, the route length of one of the pair of second routes R2 of the first bending joint 27 becomes short, the one second route R2 being a route through which the part of the first bending joint operating cable 41 which part extends from the intermediate portion to the one end portion 41a is inserted. Thus, the first bending joint 27 performs the bending operation of bending toward a side where the one second route R2 is located. Further, a part of the first bending joint operating cable 41 which part extends from the intermediate portion to the other end portion 41a is sent out to be sent into the other second route R2 which is increased in the route length out of the pair of second routes R2.

On the other hand, when the intermediate portion of the first bending joint operating cable 41 is moved toward the other side in the extending direction of the first bending joint operating cable 41 by the driving force of the driving portion 3, the part of the first bending joint operating cable 41 which part extends from the intermediate portion to the other end portion 41a is pulled, and the other end portion 41a moves toward the proximal end 21a of the arm 21. With this, the route length of the other of the pair of second routes R2 of the first bending joint 27 becomes short, the other second route R2 being a route through which the part of the first bending joint operating cable 41 which part extends from the intermediate portion to the other end portion 41a is inserted. Thus, the first bending joint 27 performs the bending operation of bending toward a side where the other second route R2 is located. Further, the part of the first bending joint operating cable 41 which part extends from the intermediate portion to the one end portion 41a is sent out to be sent into the one second route R2 which is increased in the route length out of the pair of second routes R2.

Figure 5B:
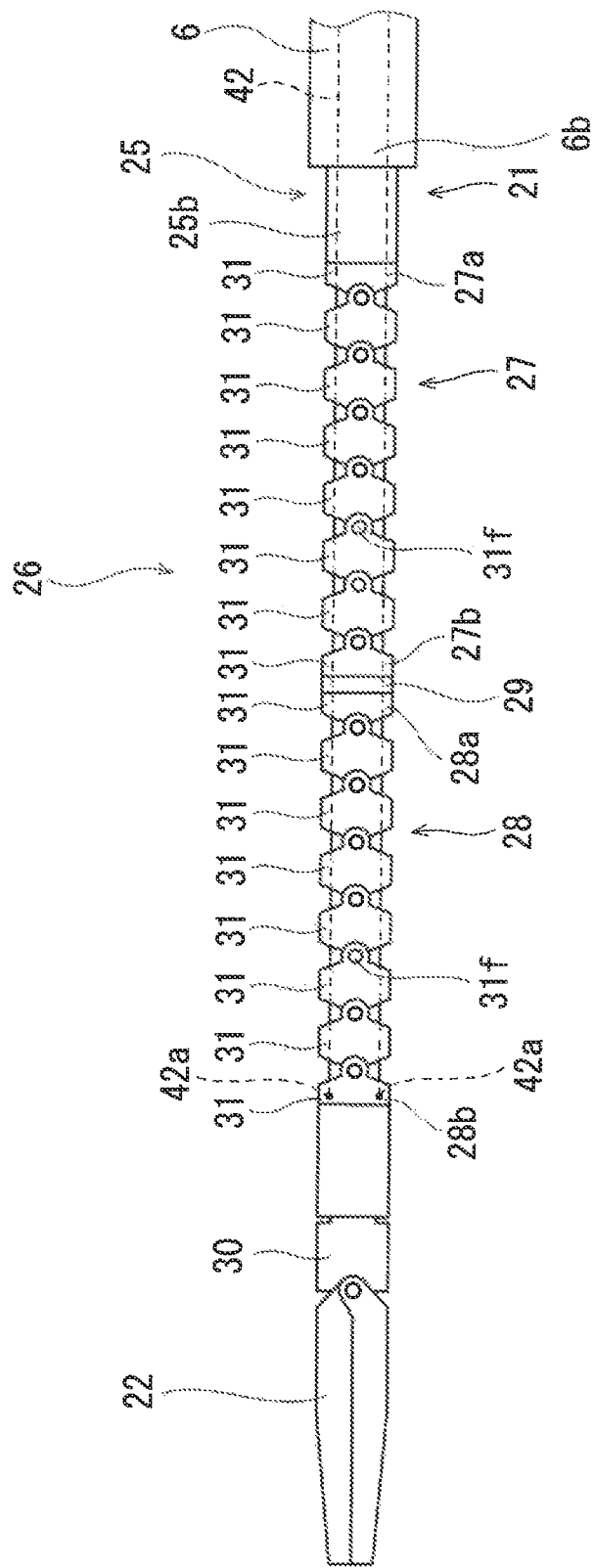
FIG. 5B is a diagram showing a configuration example of the distal end of the robot main body of the surgical robot of FIG. 1 and is a diagram showing a configuration example of a second bending joint operating cable.

FIG. 5B is a diagram showing a configuration example of the distal end of the robot main body 2 and is a diagram showing a configuration example of the second bending joint operating cable 42.

As shown in FIG. 5B, both end portions 42a of the second bending joint operating cable 42 are fixed to the frame member 31 located at the distal end 28b of the second bending joint 28. A part of the second bending joint operating cable 42 which part extends from one of the end portions 42a to a proximal end of the second bending joint operating cable 42 extends through an internal space of one of the pair of third routes R3 of the second bending joint 28, an internal space of the connecting portion 29, an internal space of one of the pair of third routes R3 of the first bending joint 27, and the internal space of the flexible shaft 25 to reach the internal space of the base 23. Further, a part of the second bending joint operating cable 42 which part extends from the other end portion 42a to an intermediate portion of the second bending joint operating cable 42 extends through an internal space of the other of the pair of third routes R3 of the second bending joint 28, the internal space of the connecting portion 29, an internal space of the other of the pair of third routes R3 of the first bending joint 27, and the internal space of the flexible shaft 25 to reach the internal space of the base 23.

The second bending joint operating cable operating portion is a mechanism provided in the base 23 and configured to move the intermediate portion of the second bending joint operating cable 42 in an extending direction of the second bending joint operating cable 42 by the driving force of the driving portion 3, the intermediate portion being located in the internal space of the base 23. When the intermediate portion of the second bending joint operating cable 42 is moved toward one side in the extending direction of the second bending joint operating cable 42 by the driving force of the driving portion 3, a part of the second bending joint operating cable 42 which part extends from the intermediate portion to one of the end portions 42a is pulled, and the one end portion 42a moves toward the proximal end 21a of the arm 21. With this, the route length of one of the pair of third routes R3 of the second bending joint 28 becomes short, the one third route R3 being a route through which the part of the second bending joint operating cable 42 which part extends from the intermediate portion to the one end portion 42a is inserted. Thus, the second bending joint 28 performs the bending operation of bending toward a side where the one third route R3 is located. Further, a part of the second bending joint operating cable 42 which part extends from the intermediate portion to the other end portion 42a is sent out to be sent into the other third route R3 which is increased in the route length out of the pair of third routes R3.

On the other hand, when the intermediate portion of the second bending joint operating cable 42 is moved toward the other side in the extending direction of the second bending joint operating cable 42 by the driving force of the driving portion 3, the part of the second bending joint operating cable 42 which part extends from the intermediate portion to the other end portion 42a is pulled, and the other end portion 42a moves toward the proximal end 21a of the arm 21. With this, the route length of the other of the pair of third routes R3 of the second bending joint 28 becomes short, the other third route R3 being a route through which the part of the second bending joint operating cable 42 which part extends from the intermediate portion to the other end portion 42a is inserted. Thus, the second bending joint 28 performs the bending operation of bending toward a side where the other third route R3 is located. Further, the part of the second bending joint operating cable 42 which part extends from the intermediate portion to the one end portion 42a is sent out to be sent into the one third route R3 which is increased in the route length out of the pair of third routes R3.

As described above, the distal end 43a of the forceps operating cable 43 is attached to the forceps 22. A part of the forceps operating cable 43 which part extends from the distal end 43a to the proximal end extends through the through hole 30a (see FIG. 4) of the wrist joint 30 and an internal space of the torque transmission tube 44 (i.e., the internal spaces of the joint portion 26 and the flexible shaft 25), and the proximal end of the forceps operating cable 43 is located in the internal space of the base 23. To be specific, the forceps operating cable 43 is inserted through the torque transmission tube 44.

The forceps operating cable operating portion is a mechanism provided in the base 23 and configured to pull the proximal end of the forceps operating cable 43 in an axial direction of the arm 21 by the driving force of the driving portion 3, the proximal end being located in the internal space of the base 23. When the proximal end of the forceps operating cable 43 is pulled by the driving force of the driving portion 3, the forceps operating cable 43 moves in an extending direction of the forceps operating cable 43, and as a result, the forceps 22 operates.

FIG. 4 is a partial breakaway view showing a configuration example of the wrist joint 30.

The torque transmission tube 44 has flexibility and is formed in a tubular shape. The torque transmission tube 44 can transmit torque, applied to the proximal end thereof, to the distal end 44a directed in an arbitrary direction. To be specific, the torque transmission tube 44 is configured such that by rotating the proximal end, the distal end 44a is rotated in accordance with a rotation amount of the proximal end through an intermediate portion thereof bent in an arbitrary shape. As shown in FIG. 4, the distal end 44a of the torque transmission tube 44 is fixed to a peripheral portion of the through hole 30a of the wrist joint 30. A part of the torque transmission tube 44 which part extends from the distal end 44a to the proximal end extends through an internal space of the first route R1 of the second bending joint 28, the internal space of the connecting portion 29, an internal space of the first route R1 of the first bending joint 27, and the internal space of the flexible shaft 25, and the proximal end of the torque transmission tube 44 is located in the internal space of the base 23.

The torque transmission tube rotating portion is a mechanism provided in the base 23 and configured to rotate the proximal end of the torque transmission tube 44 by the driving force of the driving portion 3. When the proximal end of the torque transmission tube 44 rotates, the distal end 44a of the torque transmission tube 44 is rotated, and this rotates the wrist joint 30.

Since the torque transmission tube 44 has flexibility, the torque transmission tube 44 is bendable together with the flexible shaft 25.

As shown in FIG. 2, the guide pipe 6 is a flexible tubular body, and the flexible shaft 25 is inserted through the guide pipe 6. In a use state shown in FIG. 2, the distal end 25*b* of the flexible shaft 25 projects from a distal end 6*b* of the guide pipe 6. Therefore, the joint portion 26 and the forceps 22 project from the distal end 6*b* of the guide pipe 6. A length of the guide pipe 6 is shorter than a length of the flexible shaft 25. Further, the guide pipe 6 is formed to have a size through which the flexible shaft 25, the joint portion 26, and the forceps 22 can be inserted. Therefore, by inserting the forceps 22, the joint portion 26, and the flexible shaft 25 into the guide pipe 6 through a proximal end 6*a* of the guide pipe 6 and sending the distal end of the robot main body 2 into the guide pipe 6, the distal end of the robot main body 2 can be sent into the guide pipe 6 toward the distal end 6*b*, and the forceps 22, the joint portion 26, and the distal end 25*b* of the flexible shaft 25 can project from the distal end 6*b* of the guide pipe 6. The guide pipe 6 is configured such that: the inserted surgical robot 1 and the inserted endoscope 101 can be smoothly moved in an extending direction of the guide pipe 6; and the inserted surgical robot 1 and the inserted endoscope 101 can be smoothly rotated around an axis of the guide pipe 6.

Further, rigidity of the guide pipe 6 in the bending direction is higher than the rigidity of the flexible shaft 25 in the bending direction. With this, it is possible to prevent a case where the guide pipe 6 deforms when the flexible shaft 25 is rotated around the axis thereof. Thus, an angular position of the flexible shaft 25 can be changed while maintaining an extending direction of the flexible shaft 25.

In the present embodiment, the guide pipe 6 is formed separately from the collectively bundling pipe 102. However, the guide pipe 6 may be formed integrally with the collectively bundling pipe 102.

Configuration Example of Driving Portion

As shown in FIG. 2, the driving portion 3 includes: the robot main body driving mechanism 51 configured to drive the robot main body 2; and a rotation translation unit 52.

The robot main body driving mechanism 51 is configured to individually drive the first bending joint operating cable operating portion, second bending joint operating cable operating portion, forceps operating cable operating portion, and torque transmission tube rotating portion (which are not shown) of the driving force transmission mechanism 24. The robot main body driving mechanism 51 and the base 23 of the robot main body 2 are configured to be detachable from each other. Therefore, when replacing the robot main body 2, the base 23 of the robot main body 2 can be detached from the robot main body driving mechanism 51, and the base 23 of the different robot main body 2 can be attached to the robot main body driving mechanism 51. Thus, the robot main body 2 can be replaced quickly.

By attaching the base 23 of the robot main body 2 to the robot main body driving mechanism 51, the robot main body driving mechanism 51 and the driving force transmission mechanism 24 are coupled to each other, and the driving force of the robot main body driving mechanism 51 is transmitted to the first bending joint 27, the second bending joint 28, the forceps 22, and the wrist joint 30 through the first bending joint operating cable operating portion, second bending joint operating cable operating portion, forceps operating cable operating portion, and torque transmission tube rotating portion of the driving force transmission mechanism 24.

The rotation translation unit 52 includes a rotation driving mechanism 53 and a translation driving mechanism 54.

The rotation driving mechanism 53 is a mechanism configured to drive the robot main body 2 such that the robot main body 2 rotates around an axis L1 of the proximal end 25*a* of the flexible shaft 25. In the present embodiment, the rotation driving mechanism 53 rotates the robot main body 2 and the robot main body driving mechanism 51 integrally around the axis L1 of the proximal end 25*a* of the flexible shaft 25. The rotation driving mechanism 53 includes a rotation driving mechanism supporting portion 61 and a rotation driving portion 62.

The rotation driving mechanism supporting portion 61 supports the robot main body driving mechanism 51 such that the robot main body driving mechanism 51 is rotatable around the axis L1 of the proximal end 25*a* of the flexible shaft 25. The rotation driving mechanism supporting portion 61 includes: a support base 60; a first supporting portion 58 supporting the robot main body driving mechanism 51 through a bearing (not shown) such that the robot main body driving mechanism 51 is rotatable around the axis L1 of the proximal end 25*a* of the flexible shaft 25; a rotating shaft 63 attached to the robot main body driving mechanism 51 and including an axis provided coaxially with the axis L1 of the proximal end 25*a* of the flexible shaft 25; and a second supporting portion 59 supporting the rotating shaft 63 through a bearing (not shown) such that the proximal end 25*a* of the flexible shaft 25 is rotatable around the axis L1.

The rotation driving portion 62 is, for example, a servo motor, and a driving gear 64 is fitted to a driving shaft of the rotation driving portion 62. The driving gear 64 meshes with a driven gear 65 fitted to the rotating shaft 63 of the rotation driving mechanism supporting portion 61. Therefore, when the driving shaft of the rotation driving portion 62 rotates, the robot main body driving mechanism 51 is rotated around the axis L1 of the proximal end 25*a* of the flexible shaft 25, and the robot main body 2 attached to the robot main body driving mechanism 51 is further rotated around the axis L1 of the proximal end 25*a* of the flexible shaft 25.

The translation driving mechanism 54 is a mechanism configured to translate the robot main body 2 in a direction along the axis L1 of the proximal end 25*a* of the flexible shaft 25. In the present embodiment, the translation driving mechanism 54 translates the robot main body 2 and the robot main body driving mechanism 51 integrally in the direction along the axis L1 of the proximal end 25*a* of the flexible shaft 25. The translation driving mechanism 54 includes a translation driving mechanism supporting portion 66, a guide rail mechanism 71, a ball screw mechanism 67, and a translation driving portion 68.

The guide rail mechanism 71 includes a guide rail 72 and a slider 73 configured to move on the guide rail 72. The guide rail 72 is a rod-shaped body provided so as to extend in parallel with the axis L1 of the proximal end 25*a* of the flexible shaft 25. Both end portions of the guide rail 72 are fixed to the translation driving mechanism supporting portion 66. The slider 73 is configured to slide on the guide rail 72. The slider 73 is attached to the support base 60 of the rotation driving mechanism supporting portion 61. With this, the rotation driving mechanism supporting portion 61 is supported by the guide rail mechanism 71 and moves forward and backward relative to the translation driving mechanism supporting portion 66 in the direction along the axis L1 of the proximal end 25*a* of the flexible shaft 25. Therefore, the robot main body driving mechanism 51 and the robot main body 2, which are attached to the translation driving mechanism supporting portion 66, can move forward and backward relative to the translation driving mechanism supporting portion 66 in the direction along the axis L1 of the proximal end 25a of the flexible shaft 25.

The ball screw mechanism 67 moves the rotation driving mechanism supporting portion 61 forward and backward relative to the translation driving mechanism supporting portion 66 in the direction along the axis L1 of the proximal end 25a of the flexible shaft 25. The ball screw mechanism 67 includes a ball screw 69 and a slider 70. The ball screw 69 is provided so as to extend in parallel with the axis L1 of the proximal end 25a of the flexible shaft 25. Both end portions of the ball screw 69 are supported by the translation driving mechanism supporting portion 66 such that the ball screw 69 is rotatable around an axis thereof. The slider 70 is configured to move forward and backward by the rotation of the ball screw 69 in an extending direction of the ball screw 69, i.e., in the direction along the axis L1 of the proximal end 25a of the flexible shaft 25. The slider 70 is attached to the support base 60 of the rotation driving mechanism supporting portion 61.

The translation driving portion 68 is, for example, a servo motor, and a driving shaft of the translation driving portion 68 is connected to the ball screw 69 through a reducer (not shown). Therefore, when the driving shaft of the translation driving portion 68 rotates, the ball screw 69 is rotated to move the slider 70 in the extending direction of the ball screw 69, i.e., in the direction along the axis L1 of the proximal end 25a of the flexible shaft 25. With this, the robot main body 2 and the robot main body driving mechanism 51 are integrally translated in the axial direction of the flexible shaft 25.

In the present embodiment, the rotation driving mechanism 53 directly supports the robot main body 2 and the robot main body driving mechanism 51, and the translation driving mechanism 54 translates the robot main body 2, the robot main body driving mechanism 51, and the rotation driving mechanism 53. However, the present embodiment is not limited to this. Instead of this, the translation driving mechanism 54 may directly support the robot main body 2 and the robot main body driving mechanism 51, and the rotation driving mechanism 53 may rotate the robot main body 2, the robot main body driving mechanism 51, and the translation driving mechanism 54.

In the present embodiment, the rotation translation unit 52 is supported by an inclination unit 55. The inclination unit 55 is a mechanism configured to adjust an inclination angle of the axis L1 of the proximal end 25a of the flexible shaft 25 relative to the operating table 111.

In the present embodiment, the inclination unit 55 includes a base 75, a hinge 76, and an inclination angle adjusting portion 77.

The base 75 is fixed to the surgical robot support base 113 (see FIG. 1).

The hinge 76 couples the translation driving mechanism supporting portion 66 to the base 75 such that the translation driving mechanism supporting portion 66 is liftable relative to the base 75 around an axis extending in a horizontal direction and a direction intersecting with the direction along the axis L1 of the proximal end 25a of the flexible shaft 25 when viewed from an upward/downward direction.

The inclination angle adjusting portion 77 is formed in a thin and long plate shape, and a base end portion of the inclination angle adjusting portion 77 is coupled to the base 75 such that the inclination angle adjusting portion 77 is swingable around an axis extending in the horizontal direction. A part of the inclination angle adjusting portion 77 which part extends from the base end portion thereof to a tip end portion thereof is provided with a plurality of through holes lined up in a row in an extending direction of the inclination angle adjusting portion 77. The translation driving mechanism supporting portion 66 includes an internal screw (not shown) threadedly engaged with a bolt (not shown). The bolt inserted through one of the through holes of the inclination angle adjusting portion 77 and the internal screw of the translation driving mechanism supporting portion 66 are threadedly engaged with each other. With this, the inclination angle of the translation driving mechanism supporting portion 66 relative to the base 75, i.e., the inclination angle of the axis L1 of the proximal end 25a of the flexible shaft 25 relative to the operating table 111 can be held at a predetermined inclination angle. On this account, the inclination angle of the axis L1 of the proximal end 25a of the flexible shaft 25 can be adjusted to an appropriate angle. Thus, the arm 21 can be smoothly sent into the guide pipe 6 and can be pulled out from the guide pipe 6.

Figure 7:
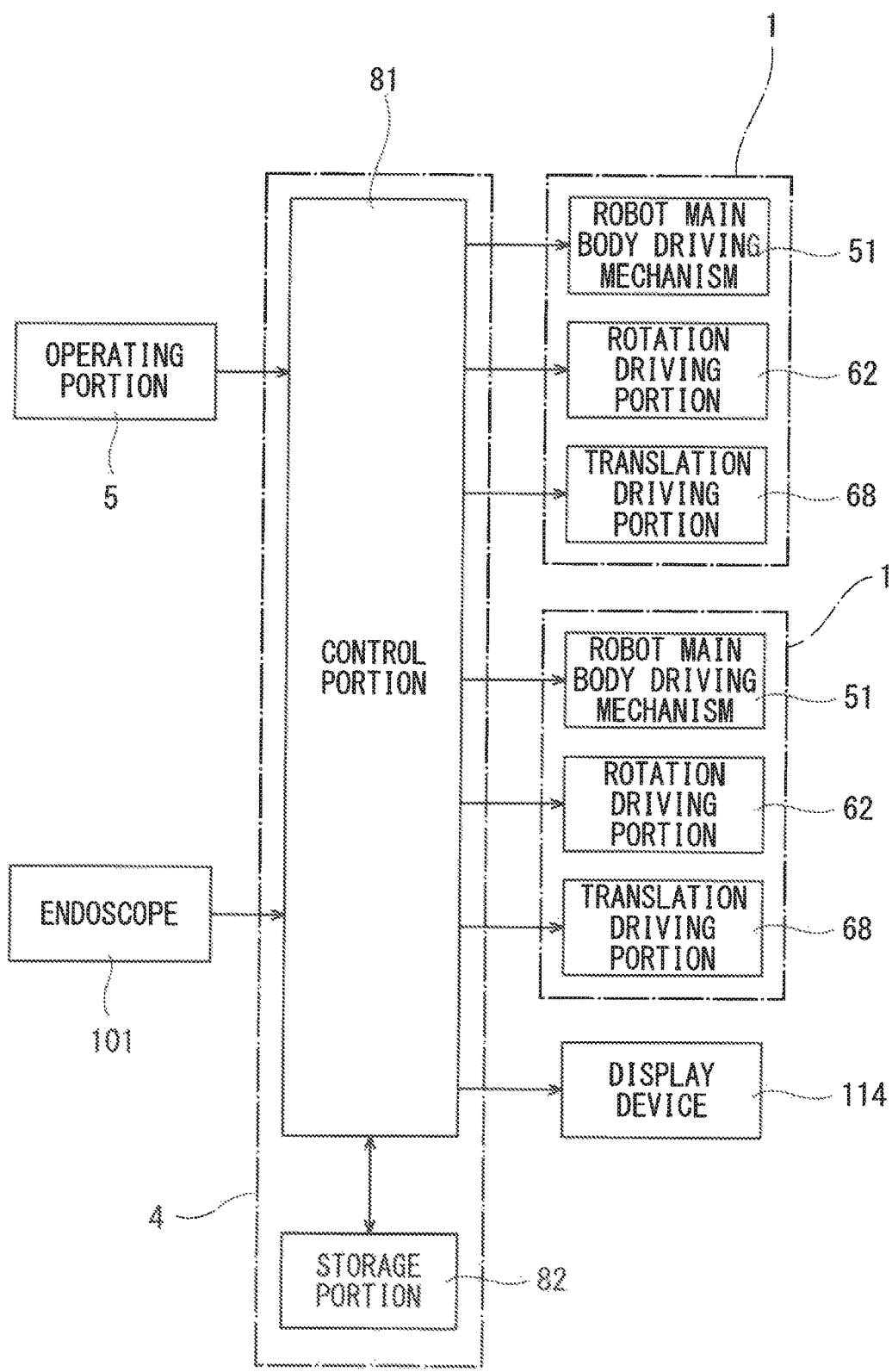
FIG. 7 is a block diagram schematically showing a configuration example of a control system of the surgical robot of FIG. 1.

Configuration Examples of Control Unit and Operating Portion FIG. 7 is a block diagram showing a configuration example of the control unit 4.

The control unit 4 included in the robot main body 2 includes: a control portion 81 including a calculation unit, such as a CPU; and a storage portion 82 including a memory, such as ROM or RAM. The control portion 81 may be constituted by a single control unit which performs centralized control or may be constituted by a plurality of control units which cooperate to perform distributed control. Based on data received from the operating portion 5, the control portion 81 controls operations of the robot main body driving mechanism 51 of the surgical robot 1, the rotation driving portion 62 of the rotation driving mechanism 53, and the translation driving portion 68 of the translation driving mechanism 54 to control an operation of the surgical robot 1. Further, the control portion 81 processes image data, received from the endoscope 101, to transmit the processed image data to the display device 114. The storage portion 82 stores predetermined control programs, and the control portion 81 reads out and executes the control programs to control the operation of the surgical robot 1.

The operator W operates the operating portion 5 to input an operation instruction to be executed by the surgical robot 1. The operating portion 5 is configured to be communicable with the control unit 4. The operating portion 5 converts the operation instruction to be executed by the surgical robot 1 into data to transmit the data to the control portion 81, the operation instruction being input by the operator W.

Example of Use

Next, an example of use of the surgical robot 1 will be explained.

Figure 8:
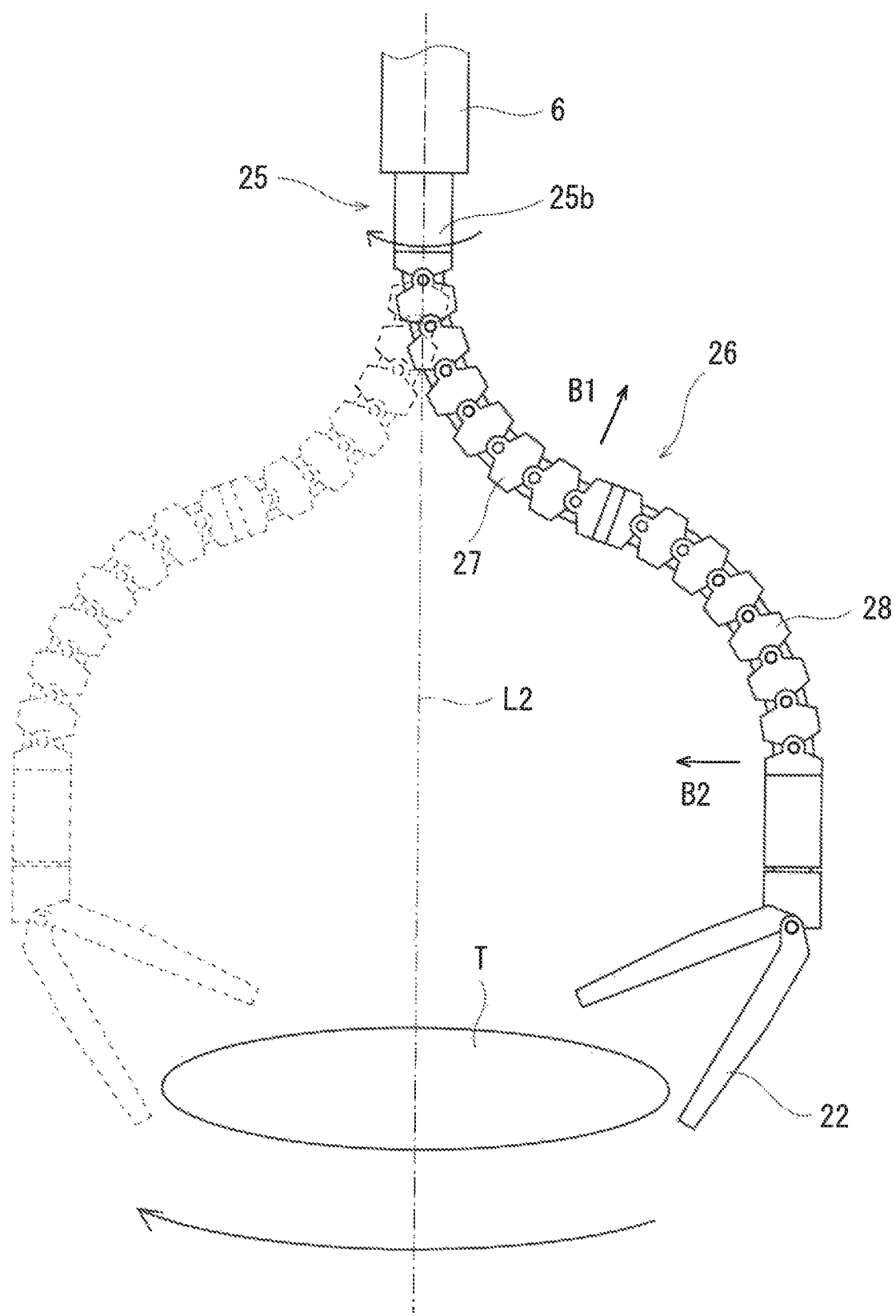
FIG. 8 is a diagram showing an operation example of the surgical robot of FIG. 1.

FIG. 8 is a diagram showing an operation example of the surgical robot 1 in the example of use.

First, as shown in FIG. 2, one or more guide pipes 6 are inserted into the collectively bundling pipe 102 through an opening of a proximal end 102a of the collectively bundling pipe 102 and are sent into the collectively bundling pipe 102 until the distal end 6b of the guide pipe 6 projects from a distal end 102b of the collectively bundling pipe 102. Similarly, the endoscope 101 is sent into the collectively bundling pipe 102 until a distal end of the endoscope 101 projects from the distal end 102b of the collectively bundling pipe 102.

Next, a trocar 110 is placed on a part of a body surface of the patient P, one or more surgical robots 1 and the endoscope 101 being inserted into the part of the body surface.

Next, the collectively bundling pipe 102 is inserted into the trocar 110 placed on the body surface of the patient P. Then, the inside of the body of the patient P is visually recognized by the endoscope 101, and the distal end 102b of the collectively bundling pipe 102 is located in the vicinity of a treated part of the patient P. The collectively bundling pipe 102, the endoscope 101, and the guide pipe 6 have flexibility. Therefore, for example, even when an organ of the patient P is located on a virtual straight line passing through the part on which the trocar 110 is placed and the treated part, the collectively bundling pipe 102, the endoscope 101, and the guide pipe 6 can be curved to bypass the organ. Thus, the distal end 102b of the collectively bundling pipe 102 can be introduced to the vicinity of the treated part.

Next, the arm 21 of the robot main body 2 of each of the one or more surgical robots 1 is inserted into the guide pipe 6 through an opening of the proximal end 6a of the guide pipe 6 and is sent into the guide pipe 6 until the distal end 21b of the arm 21 projects from the distal end 6b of the guide pipe 6. With this, the one or more surgical robots 1 and the endoscope 101 can be collectively bundled by the collectively bundling pipe 102 to be integrally introduced to the vicinity of the treated part of the patient P.

Next, the base 23 is attached to the robot main body driving mechanism 51, and with this, the driving force transmission mechanism 24 of the robot main body 2 and the robot main body driving mechanism 51 are coupled to each other. Thus, the driving force of the robot main body driving mechanism 51 is transmitted to the first bending joint 27, the second bending joint 28, the forceps 22, and the wrist joint 30 through the first bending joint operating cable operating portion, second bending joint operating cable operating portion, forceps operating cable operating portion, and torque transmission tube rotating portion of the driving force transmission mechanism 24. Then, the inclination unit 55 is operated to adjust the inclination angle of the axis L1 of the proximal end 25a of the flexible shaft 25 relative to the operating table 111 to an appropriate angle.

Next, the operator W operates the operating portion 5 while confirming the image taken by the video camera of the endoscope 101 and displayed on the display device 114. Then, based on the data received from the operating portion 5, the control portion 81 controls the operations of the robot main body driving mechanism 51, the rotation driving portion 62 of the rotation driving mechanism 53, and the translation driving portion 68 of the translation driving mechanism 54 to control the operation of the surgical robot 1.

At this time, when the control portion 81 determines that the operation instruction to be executed by the surgical robot 1 contains an operation instruction of moving the forceps 22 in the radial direction about the axis L2 of the distal end 25b of the flexible shaft 25, the control portion 81 drives the robot main body driving mechanism 51 to bend the first bending joint 27 and the second bending joint 28. With this, the forceps 22 moves in the radial direction about the axis L2 of the distal end 25b of the flexible shaft 25.

Further, when the control portion 81 determines that the operation instruction to be executed by the surgical robot 1 contains an operation instruction of moving the forceps 22 in a circumferential direction about the axis L2 (see FIGS. 3 and 4) of the distal end 25b of the flexible shaft 25, the control portion 81 drives the rotation driving portion 62 of the rotation translation unit 52 to rotate the proximal end of the flexible shaft 25 around the axis L1. With this, as shown in FIG. 8, the entire flexible shaft 25 rotates around the axis of the flexible shaft 25 in an internal space of the guide pipe 6 while maintaining the posture of the flexible shaft 25 in the axial direction. As a result, the joint portion 26 that is continuous with the distal end 25b of the flexible shaft 25 rotates around the axis L2 of the distal end 25b of the flexible shaft 25. To be specific, for example, when the first bending joint 27 is bent in a direction B1, and the second bending joint 28 is bent in a direction B2 opposite to the direction B1, the forceps 22 moves on a circumference about the axis L2 of the distal end 25b of the flexible shaft 25. Therefore, the operator W can operate the operating portion 5 to change a position where the forceps 22 holds the target.

Further, when the control portion 81 determines that the operation instruction to be executed by the surgical robot 1 contains an operation instruction of changing a projection amount of the distal end of the surgical robot 1 projecting from the distal end of the guide pipe 6, the control portion 81 drives the translation driving portion. 68 of the rotation translation unit 52 to move the robot main body 2 in the direction along the axis L1 of the proximal end 25a of the flexible shaft 25.

With this, the flexible shaft 25 is sent (inserted) into the guide pipe 6 or pulled out from the guide pipe 6. By sending the arm 21 into the guide pipe 6, the projection amount of the distal end of the surgical robot 1 projecting from the distal end of the guide pipe 6 can be increased, and the forceps 22 can be moved close to, for example, the treated part of the patient P. Further, by pulling out the arm 21 from the guide pipe 6, the projection amount of the distal end of the surgical robot 1 projecting from the distal end of the guide pipe 6 can be reduced, and the forceps 22 can be moved away from, for example, the treated part of the patient P. As above, the operator W can operate the operating portion 5 to change the projection amount of the distal end of the surgical robot 1 projecting from the distal end of the guide pipe 6 and move the forceps 22 in a direction along the axis L2 of the distal end 25b of the flexible shaft 25.

As described above, when the control portion 81 determines that the operation instruction to be executed by the surgical robot 1 contains the operation instruction of moving the forceps 22 in the radial direction about the axis L2 of the distal end 25b of the flexible shaft 25, the control portion 81 drives the robot main body driving mechanism 51 to bend the first bending joint 27 and the second bending joint 28. At this time, the forceps 22 is moved close to the flexible shaft 25 in the direction along the axis L2 of the distal end 25b of the flexible shaft 25. To cancel this movement, the control portion 81 may send the arm 21 into the guide pipe 6 in accordance with a movement distance of the forceps 22 moved close to the flexible shaft 25 in the direction along the axis L2 of the distal end 25b of the flexible shaft 25 when the operation of bending the first bending joint 27 and the second bending joint 28 is performed. With this, the forceps 22 can be moved in a plane perpendicular to the direction along the axis L2 of the distal end 25b of the flexible shaft 25.

When replacing a certain surgical tool with a different surgical tool during surgery, the base 23 is detached from the robot main body driving mechanism 51, and the surgical robot 1 including the certain surgical tool is pulled out from the guide pipe 6. Then, the surgical robot 1 including the different surgical tool is inserted into the guide pipe 6. As above, a part of the surgical tools can be replaced while maintaining the position of the other surgical robot including the surgical tool other than the surgical tool to be replaced and the position of the endoscope 101 in the vicinity of the treated part. Therefore, the surgical tool can be replaced quickly, and load on the body of the patient P can be reduced. Further, workload on the operator W can be reduced.

As described above, the surgical robot 1 of the present invention can rotate the robot main body 2 around an axis of the proximal end 21a of the arm 21 by the rotation driving mechanism 53 and move the forceps 22 in the circumferential direction about the axis L2 of the distal end 25b of the flexible shaft 25. To be specific, the forceps 22 can be moved in the circumferential direction about the axis L2 of the distal end 25b of the flexible shaft 25 without translating the proximal end 21a of the atm 21 in a three-dimensional space. Therefore, a large-scale apparatus for translating the proximal end 21a of the arm 21 in the three-dimensional space is not required. Therefore, the surgical robot 1 can be reduced in size, and the manufacturing cost of the surgical robot 1 can be made low.

From the foregoing explanation, many modifications and other embodiments of the present invention are obvious to one skilled in the art. Therefore, the foregoing explanation should be interpreted only as an example and is provided for the purpose of teaching the best mode for carrying out the present invention to one skilled in the art. The structures and/or functional details may be substantially modified within the scope of the present invention.

REFERENCE SIGNS LIST

L1 axis
L2 axis
O operator
P patient
W operator
1 surgical robot
2 robot main body
3 driving portion
4 control unit
5 operating portion
6 guide pipe
21 area
22 forceps
22a operating shaft
23 base
24 driving force transmission mechanism
25 flexible shaft
26 joint portion
27 first bending joint
28 second bending joint
29 connecting portion
30 wrist joint
30a through hole
31 frame member
32 operating cable coupling portion
33 operating cable coupling portion
41 first bending joint operating cable
42 second bending joint operating cable
43 forceps operating cable
44 torque transmission tube
51 robot main body driving mechanism
52 rotation translation unit
53 rotation driving mechanism
54 translation driving mechanism
55 inclination unit
58 first supporting portion
59 second supporting portion
60 support base
61 rotation driving mechanism supporting portion
62 rotation driving portion
63 rotating shaft
64 driving gear
65 driven gear
66 translation driving mechanism supporting portion
67 ball screw mechanism
68 translation driving portion
69 ball screw
70 slider
71 guide rail mechanism
72 guide rail
73 slider
75 base
76 hinge
77 inclination angle adjusting portion
81 control portion
82 storage portion
100 surgical robot system
111 operating table
112 support rail
113 surgical robot support base

The invention claimed is:
1. A surgical robot system comprising:
a first robot main body that includes a first base, a first flexible shaft having a proximal end connected to the first base, a first bending joint connected to the first flexible shaft, a first wrist joint connected to the first bending joint, a first end effector connected to the first wrist joint, and a first driving force transmitter including a first cable connected to the first bending joint and a first torque transmission tube connected to the first wrist joint;
a second robot main body that includes a second base, a second flexible shaft having a proximal end connected to the second base, a second bending joint connected to the second flexible shaft, a second wrist joint connected to the second bending joint, a second end effector connected to the second wrist joint, and a second driving force transmitter including a second cable connected to the second bending joint and a second torque transmission tube connected to the second wrist joint;
a first robot main body driver having a first surface for attachment to the first base of the first robot main body;
a second robot main body driver having a second surface for attachment to the second base of the second robot main body;
a first support base rotatably supporting the first robot main body driver around an axis of a proximal end of the first flexible shaft;
a second support base placed away from the first support base in a direction different from a direction of the axis of the proximal end of the first flexible shaft and rotatably supporting the second robot main body driver around an axis of a proximal end of the second flexible shaft;
a first rotation driver supported by the first support base and configured to rotate the first robot main body driver with which the first robot main body is attached around the axis of the proximal end of the first flexible shaft; and
a second rotation driver supported by the second support base and configured to rotate the second robot main body driver with which the second robot main body is attached around the axis of the proximal end of the second flexible shaft, wherein
the first torque transmission tube rotates around an axis of the first torque transmission tube and transmits the driving force of the first robot main body driver to the first wrist joint, the first wrist joint rotates about an axis of a distal end of the first torque transmission tube by the rotation of the first torque transmission tube, the second torque transmission tube rotates around an axis of the second torque transmission tube and transmits the driving force of the second robot main body driver to the second wrist joint, and the second wrist joint rotates about an axis of a distal end of the second torque transmission tube by the rotation of the second torque transmission tube.

2. The surgical robot system according to claim 1, comprising
a first supporting portion that movably supports the first support base; and
a first translation driver supported by the first supporting portion and configured to translate the first support base in the direction of the axis of the proximal end of the first flexible shaft.

3. The surgical robot system according to claim 2, further comprising
a first guide rail supported by the first supporting portion and extending in the direction of the axis of the proximal end of the first flexible shaft; and
a first slider moving along the first guide rail and attached to the first support base.

4. The surgical robot system according to claim 2, further comprising
a second supporting portion that movably supports the second support base; and
a second translation driver supported by the second supporting portion and configured to translate the second support base in a direction of the axis of the proximal end of the second flexible shaft.

5. The surgical robot system according to claim 4, further comprising
a second guide rail supported by the second supporting portion and extending in the direction of the axis of the proximal end of the second flexible shaft; and
a second slider moving along the second guide rail and attached to the second support base.

6. The surgical robot system according to claim 1, wherein:
the first robot main body further includes a third bending joint connected to the first bending joint;
the first driving force transmitter further includes a third cable which connects the third bending joint and transmits a driving force of the first robot main body driver to the third bending joint;
the first bending joint receives the driving force of the first robot main body driver to perform a bending operation in a predetermined direction; and
the third bending joint receives the driving force of the first robot main body driver to perform a bending operation in a direction opposite to the direction in which the first bending joint performs the bending operation.

7. The surgical robot system according to claim 1, wherein the first end effector is a pair of forceps, and the second end effector is a pair of forceps.

8. The surgical robot system according to claim 1, wherein the first support base has a longitudinal direction parallel to the axis of the proximal end of the first flexible shaft, and the second support base has a longitudinal direction parallel to the axis of the proximal end of the second flexible shaft.

9. The surgical robot system according to claim 1, wherein the first driving force transmitter includes a first end effector operating cable which connects the first end effector and transmits a driving force of the first robot main body driver attached via the first base to the first end effector, the first end effector operating cable being disposed within the first torque transmission tube.

10. The surgical robot system according to claim 1, wherein
the first cable transmits a driving force of the first robot main body driver to the first bending joint,
the first cable and the first torque transmission tube are disposed inside of the first bending joint and extend parallel to each other.

* * * * *